United States Patent [19]

Stephen et al.

[11] Patent Number: 4,613,638
[45] Date of Patent: Sep. 23, 1986

[54] HINDERED PHENOLIC COMPOUNDS DERIVED FROM HEXIDES AND STABILIZED COMPOSITIONS

[75] Inventors: John F. Stephen, West Chester, Pa.; Jerry H. Smith; Makram H. Meshreki, both of Wilmington, Del.

[73] Assignee: ICI Americas Inc., Wilmington, Del.

[21] Appl. No.: 766,500

[22] Filed: Aug. 19, 1985

[51] Int. Cl.$^4$ .................. C07D 493/14; C08K 5/15
[52] U.S. Cl. .................................. 524/109; 524/120; 524/126; 524/304; 549/464; 252/57
[58] Field of Search .................. 524/109; 549/464; 252/57

[56] References Cited

U.S. PATENT DOCUMENTS

| | | | |
|---|---|---|---|
| 2,967,169 | 1/1961 | Oberdorfer | 524/109 |
| 3,285,855 | 11/1966 | Dexter et al. | 524/291 |
| 3,962,313 | 6/1976 | Dexter et al. | 524/291 |

Primary Examiner—Veronica P. Hoke
Attorney, Agent, or Firm—Richard A. Rowe

[57] ABSTRACT

Novel phenolic compounds derived from hexides are disclosed which are useful stabilizers of synthetic polymer resins.

7 Claims, No Drawings

HINDERED PHENOLIC COMPOUNDS DERIVED FROM HEXIDES AND STABILIZED COMPOSITIONS

The present invention relates to novel hindered phenolic compounds derived from hexides and to stabilized polymer resins containing these materials. It also relates to resins containing the novel stabilizers with costabilizers including thio-synergist and phosphites.

The compounds of this invention have the following general formula: $C_6H_8O_4R_2$ wherein R is:

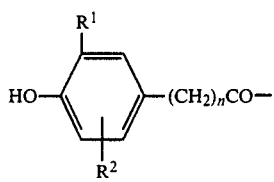

wherein $R^1$ and $R^2$ are independently H or alkyl groups of from 1 to 8 carbon atoms or cyclo alkyl groups having from 5-12 carbon atoms, n has a value of 1-6, and $C_6H_8O_4$ is a hexide moiety also referred to as a hexitol dianhydride.

Examples of such hexides include 1,4:3,6-dianhydro-D-mannitol(isomannide); 1,4:3,6-dianhydro-D-sorbitol-(isosorbide); 1,4:3,6-dianhydro-L-iditol (isoidide): and 1,5:3,6-dianhydro-D-mannitol(neomannide).

The preferred hexide is derived from the anhydrization of sorbitol to form isosorbide. The preferred compound has $R^1=R^2=$t-butyl n=2, and $C_{6H8}O_4)=$1,4:3,6-dianhydro-D-soribtol, as follows:

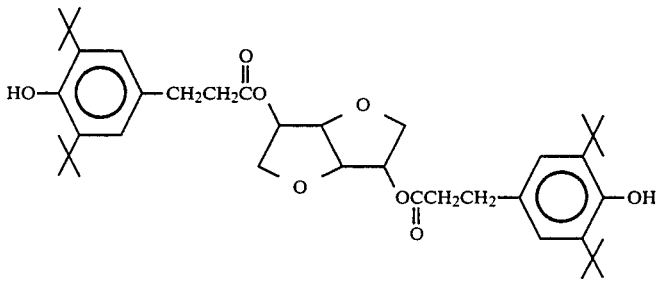

The invention relates to hindered phenolic esters derived from individual hexides as well as mixtures containing more than one hexide.

U.S. Pat. No. 2,967,169 discloses a stabilizer containing isosorbide or an ether or ester derivative of isosorbide having a hydrocarbon group. The compounds of the instant invention differ significantly in that they contain a hindered phenolic group which imparts improved functionality. The compounds of the present invention are unexpectedly superior to those of the prior art.

The compounds of the invention are prepared by transesterification of the hexide with a lower alkyl ester containing the hindered phenol group in the presence of a suitable catalyst. The hexides are prepared by anhydrization of hexitols using the methods known in the literature such as: R. L. Hockett et al, J. Am. Chem. Soc., 68, 927,930(1946) and U.S. Pat. No. 3,454,603. The lower alkyl esters containing the hindered phenolic group are prepared by methods described in U.S. Pat. Nos. 3,330,859 and 3,364,250. Suitable catalyst include sodium methoxide, lithium hydride, potassium carbonate and lithium amide. The preferred catalyst is sodium methoxide.

The compounds of this invention are stabilizers of organic material normally subject to thermal and oxidative deterioration. Materials which are thus stabilized include synthetic organic polymeric substances such as vinyl resins formed from the polymerization of ethylenically unsaturated monomers such as vinyl halides with unsaturated polymerizable compounds for example vinylesters, α, β-unsaturated keytones, α,β-unsaturated aldehydes, and unsaturated hydrocarbons such as butadienes and styrene; poly-α-olefins, polyurethanes and polyamides such as polyhexamethylene adipamide and polycaprolactam: polyesters such as polyethylene terephthalates: polycarbonates; polyacetals: polystyrene; polyethyleneoxide; polyisoprene; polybutadiene and copolymer such as those of high impact polystyrene containing copolymers of butadiene and styrene and those formed by the copolymerization of acrylonitrile, butadiene and/or styrene.

In general, one or more of the stabilizers of the present invention are employed in amounts ranging from 0.005 to about 5% by weight of the compositions to be stabilized. A particularly advantageous range of the present stabilizers is from about 0.05% to about 2% by weight. The preferred range is particularly effective in polyolefins such as polypropylene.

These compounds may be incorporated in the polymer substance during the usual processing operations, for example, by milling, or extrusion. The stabilized polymer can be fabricated into films, filaments, hollow-spheres and the like. The heat stabilizing properties of these compounds advantageously stabilize the polymer against degradation during such processing at the high temeratures generally encountered.

The stabilizers employed in this invention can be used in combination with other stabilizers or additives. Especially useful co-stabilizers are dilauryl-β-thiodipropionate (DLTDP) and distearyl-β-thiodipropionate (DSTDP).

The stabilizers described in this invention can be used in combination with di-and tri-alkyl and alkyl phenyl phosphites such as tris-nonylphenyl phosphite, tris(2,4-di-tert-butylphenyl)phosphite, bis(2,4-di-t-butylphenyl)pentaerythritol diphosphite, tetrakis(2,4-di-tert-butylphenyl)-4,4'-biphenylene diphosphonite, and distearyl pentaerythritol disphosphite.

Other antioxidants, antiozonants, thermal stabilizers, ultraviolet light absorbers, coloring materials, dyes, pigments, metal chelating agents, etc., may also be used in the compositions in combination with the stabilizers of the invention.

The following examples serve to illustrate but not limit the scope of the invention. All proportions referred to therein are by weight unless otherwise specified.

EXAMPLE 1

Isorbide bis [3-(3,5-di-tert-butyl]-4-hydroxyphenyl)-propionate]

Methyl 3-(3,5-di-tert-butyl-4-hydroxyphenyl) propionate (7.01 g) was added to a flask equipped with a reflux condenser heated with hot water (60° C.). The material was heated to 155° C. under $N_2$ with magnetic stirring. Sodium methoxide (0.054 g) was added and a vacuum (1mm) was applied. After 15 min., the vacuum was broken with $N_2$, isosorbide (1.46 g) was added, and the vacuum was reapplied. After 5 hrs., the reaction was quenched with acetic acid, dissolved in ethyl acetate, and extracted with water. Excess starting ester was removed by vacuum distillation. The glassy residue was crushed to give 6.27 g (95%) of the desired product, m.p. 55°-60° C.

Calculated for $C_{40}H_{58}O_8$: C, 72.04; H, 8.77. Found: C, 71.68; H, 9.03.

EXAMPLE 2

This example shows the usefulness of the invention for stabilization of polypropylene. The stabilizers were incorporated into Profax 6301 TM polypropylene resin by solvent blending (methylene chloride) followed by extrusion at 200° C. Twenty-five mil plaques were prepared by compression molding at 6,000 psi and 188° C. Samples were tested in a forced draft oven at 150° C. Failure was determined when the first signs of decomposition were observed. Tests were run in quadruplicate and an average value was determined. Results are shown in Table I.

TABLE I

| Stabilizer | Concentration (%) | Hours to Failure |
|---|---|---|
| none | — | 24 |
| Ex 1 | 0.10 | 522 |
| Ex 1/DSTDP | 0.10/0.25 | 1680 |

EXAMPLE 3

This example shows the usefulness of the invention for stabilization of high impact polystyrene. The stabilizers were incorporated into high impact polystyrene by milling at 188° C. Twenty mil plaques were prepared by compression molding at 6,000 psi and 188° C. Samples were tested in a forced draft oven at 90° C. Failure was determined when cracking was observed after flexing the plaque over a one-inch mandrel. Tests were run in quadruplicate and an average value was determined. Results are shown in Table II.

TABLE II

| Stabilizer | Concentration (%) | Hours to Failure |
|---|---|---|
| none | — | 48 |
| Ex 1 | 0.10 | 328 |
| Ex 1/DLTDP | 0.05/0.15 | 232 |

EXAMPLE 4

This example shows the usefulness of the invention for stabilization of high density polyethylene. The stabilizers were incorporated into high density polyethylene (Allied Chemical EA 55-003) by solvent blending (methylene chloride) followed by extrusion at 230° C. Twenty-five mil plaques were prepared by compression molding at 6,000 psi and 188° C. Samples were tested in a forced draft oven at 120° C. Failure was determined when cracking was observed after flexing. Tests were run in quadruplicate and an average value was determined. Results are shown in Table III.

TABLE III

| Stabilizer | Concentration (%) | Hours to Failure |
|---|---|---|
| none | — | 48 |
| Ex 1 | .05 | 3288 |
| Ex 1/Weston 618 | .025/.05 | 3624 |

What is claimed is:

1. A hindered phenolic compound derived from a hexide having the general formula:

$$C_6H_8O_4R_2$$

wherein R has the following general formula:

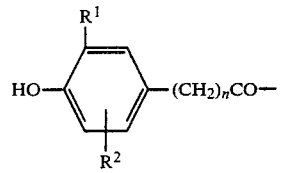

wherein $R^1$ and $R^2$ are independently hydrogen or alkyl groups of from 1-8 carbon atoms or cycloalkyl groups having from 5-12 carbon atoms, n has a value of 1-6 and $C_6H_8O_4$ is a hexide structure.

2. A compound of claim 1 wherein $R^1$ and $R^2$ are tert-butyl groups and $R^2$ is ortho to the hydroxyl.

3. A compound of claim 2 wherein n=2.

4. A compound of claim 3 wherein said hexide is 1,4:3,6-dianhydro-D-sorbitol.

5. An organic material normally subject to thermal and oxidative deterioration containing from 0.005-5% by weight of a compound of claim 1.

6. A composition of claim 5 comprising a resin selected from the group consisting polyethylene, polypropylene and polystyrene.

7. A composition of claim 6 further comprising a costabilizer compound selected, from the group consisting of dilauryl-β-thiodipropionate, distearyl-β-thiodipropionate, distearyl pentaerythritol diphosphite, pentaerythritol tetrakis (3-(dodecylthio)propionate), tris(2,4-di-tert-butylphenyl)phosphite, bis(2,4-di-tert-butylphenyl)pentaerythritol diphosphite, and tetrakis(2,4-di-tert-butylphenyl)4,4'-biphenylene diphosphonite.

* * * * *